US010558783B2

(12) United States Patent
Ahmed et al.

(10) Patent No.: US 10,558,783 B2
(45) Date of Patent: Feb. 11, 2020

(54) IMAGE DATA INGESTION APPLICATION OF A MEDICAL IMAGING DATA PROCESSING AND RETRIEVAL SYSTEM

(71) Applicant: MEDSTREAMING, INC., Redmond, WA (US)

(72) Inventors: Ahmed Aly Saad Ahmed, Redmond, WA (US); Evert de Vries, Redmond, WA (US); Wael Elseaidy, Redmond, WA (US)

(73) Assignee: MEDSTREAMING, INC., Redmond, WA (US)

( * ) Notice: Subject to any disclaimer, the term of this patent is extended or adjusted under 35 U.S.C. 154(b) by 438 days.

(21) Appl. No.: 15/339,924

(22) Filed: Oct. 31, 2016

(65) Prior Publication Data

US 2017/0235913 A1 Aug. 17, 2017

Related U.S. Application Data

(60) Provisional application No. 62/249,106, filed on Oct. 30, 2015.

(51) Int. Cl.
*G06F 19/00* (2018.01)

(52) U.S. Cl.
CPC .................. *G06F 19/321* (2013.01)

(58) Field of Classification Search
USPC .................. 382/128, 131–132, 305; 705/2–3
See application file for complete search history.

(56) References Cited

U.S. PATENT DOCUMENTS

| 6,017,307 A | 1/2000 | Raines |
| 6,690,397 B1 | 2/2004 | Daignault, Jr. |
| D533,875 S | 12/2006 | Miles et al. |
| 7,693,315 B2 * | 4/2010 | Krishnan ............... G06T 7/0012 382/100 |

(Continued)

OTHER PUBLICATIONS

Notice of Allowance (U.S. Appl. No. 29/641,354), dated Sep. 25, 2018—7 pages.

(Continued)

*Primary Examiner* — Ishrat I Sherali
(74) *Attorney, Agent, or Firm* — Han Santos, PLLC; Nabil Abdalla (57) ABSTRACT

This disclosure describes techniques that relate generally to the collection, processing, storage, and graphical representation of medical imaging data associated with patient care. Medical imaging data may be processed using object recognition algorithms to help determined pertinent medical characteristics. Further, a graphical fusion application may generate a graphical representation of medical data that is based at least in part on a combination of medical imaging data and corresponding interpretation data. The graphical representation may overlay a schematic diagram of a relevant organ system, so as to provide a medical practitioner with a visual, more specifically graphical, indication of the medical imaging data. Interpretation data of pertinent medical characteristics may be generated by an automated analysis of the medical imaging data. Further, the medical imaging data along with corresponding interpretation data may be graphically overlaid onto a schematic diagram of the relevant organ system to facilitate review of medical imaging data.

20 Claims, 8 Drawing Sheets

(56) References Cited

U.S. PATENT DOCUMENTS

| | | | |
|---|---|---|---|
| 7,912,528 B2* | 3/2011 | Krishnan | G16H 50/20 |
| | | | 600/407 |
| 9,002,075 B2* | 4/2015 | Niwa | G06Q 50/24 |
| | | | 382/128 |
| 9,180,302 B2 | 11/2015 | Drees et al. | |
| D752,622 S | 3/2016 | Cojuangco et al. | |
| 9,392,953 B1 | 7/2016 | Gharib | |
| D769,278 S | 10/2016 | Ukrainsky et al. | |
| D777,191 S | 1/2017 | Polimeni | |
| D828,365 S | 9/2018 | Elseaidy et al. | |
| 10,176,896 B2* | 1/2019 | Sharma | G16H 30/20 |
| 2002/0049375 A1 | 4/2002 | Strommer et al. | |
| 2002/0182186 A1 | 12/2002 | Loeb | |
| 2004/0107118 A1* | 6/2004 | Harnsberger | G06F 17/24 |
| | | | 705/2 |
| 2008/0212856 A1* | 9/2008 | Oosawa | G06F 19/321 |
| | | | 382/128 |
| 2008/0249807 A1* | 10/2008 | Niwa | G06F 19/321 |
| | | | 705/3 |
| 2009/0022387 A1 | 1/2009 | Shirahata et al. | |
| 2015/0173707 A1 | 6/2015 | Ohuchi et al. | |
| 2015/0324522 A1* | 11/2015 | Chan | G06F 19/321 |
| | | | 705/3 |
| 2015/0342537 A1 | 12/2015 | Taylor et al. | |
| 2016/0335394 A1* | 11/2016 | Kawagishi | G06F 19/321 |

OTHER PUBLICATIONS

Notice of Allowance (U.S. Appl. No. 29/641,365), dated Sep. 25, 2018—7 pages.
Notice of Allowance (U.S. Appl. No. 29/641,370)—dated Sep. 25, 2018—7 pages.
Ex Parte Office Action for Design U.S. Appl. No. 29/582,913, dated Jan. 16, 2018—6 pages.
Restriction Requirement Office Action for Design U.S. Appl. No. 29/582,913, dated Oct. 6, 2017—5 pages.
Notice of Allowance for Design U.S. Appl. No. 29/582,913, dated May 9, 2018—7 pages.
Notice of Allowance for Design U.S. Appl. No. 29/641,359, dated Sep. 19, 2018—7 pages.

* cited by examiner

FIG. 4B
(Detail A of FIG. 4A)

FIG. 4C
(Detail B of FIG. 4A)

IMAGE DATA INGESTION APPLICATION OF A MEDICAL IMAGING DATA PROCESSING AND RETRIEVAL SYSTEM

RELATED APPLICATIONS

This application claims priority to a commonly owned U.S. Provisional Patent Application No. 62/249,106 filed on Oct. 30, 2015, and titled "Graphical Fusion Work Flow and Clinical Data Management System," which is herein incorporated by reference in its entirety.

BACKGROUND

Present day, clinical data management is becoming an increasingly crucial aspect of facilitating patient-specific care and conducting research to understand different abnormality and disease processes across populations. Medical practitioners are often burdened with the task of navigating through onerous and complicated information infrastructure. Often, a complete patient history may be difficult to discern because of the plethora of medical data, and format in which it is presented. While collecting raw data from disparate systems is only the beginning, present day systems often lack technical capabilities in distilling the information in such a way that it may focus on a specific questions or strategy that enables a medical practitioner to discover more meaningful insights that relate to patient specific care, or population trends when dealing with different abnormalities and diseases.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

This disclosure describes techniques that relate generally to the collection, processing, storage and a graphical representation of medical imaging data associated with patient care. Medical imaging data may relate to image data that is generated by medical imaging devices such as, but not limited to, x-ray, magnetic resonance imaging (MM), computed tomography (CT), ultrasound, and Positron Emission Tomography (PET). The medical imaging data may be further processed using at least one interpretation tool, such as object recognition algorithms—more specifically, optical characteristic recognition, feature-based and appearance-based methods. A database is configured to store interpretation data generated as part of processing the medical imaging data. Further, a graphical fusion application may generate a graphical representation of medical data that is based at least in part on a combination of medical imaging data and corresponding interpretation data.

The disclosure describes techniques that includes analyzing and aggregating medical imaging data that is received from one or more medical imaging device(s). The techniques further describe generating interpretation data that is based on an automated analysis of the medical imaging data. Further, the medical imaging data along with corresponding interpretation data may be presented on a user interface of a client device. In some examples, the medical imaging data may be graphically overlaid onto a schematic diagram of the relevant organ system. For example, medical imaging data associated with a cerebrovascular system of a particular patient may be analyzed to quantify a percentage of stenosis due to plaque buildup at a particular point along the carotid artery. The stenosis may be graphically represented as a constriction of the carotid artery. Further, the graphical representation may illustrate a partial constriction, or an occlusion, based at least in part on the percentage of stenosis derived from an analysis of the medical imaging data. For example, a stenosis of forty-percent at a particular point along the carotid artery may be graphically represented at the particular point as a forty-percent constriction of the carotid artery.

The disclosure further describes a graphical fusion application that may facilitate a review of medical imaging data. In some examples, the graphical fusion application, via a user interface instruction from a client device, may access medical imaging data and interpretation data of such, from a data-store associated with the image data processing and retrieval system. Preferably, the retrieval of the medical imaging data may include interpretation data of pertinent medical characteristics. In some examples, the retrieval of medical imaging data may include a temporal sequence of medical imaging data performed on a same anatomical organ system over a predetermined period of time. In some examples, the graphical fusion application may present the temporal sequence of medical imaging data along with associated interpretation data.

In some examples, the graphical fusion application may generate a graph that represents changes in pertinent medical characteristics over a predetermined period of time. For example, changes in blood flow velocity (i.e., PSV or ESV), or stenosis may be graphed over a predetermined period of time, based on the availability of the relevant medical imaging data. The graphical fusion application may generate one or more graphs based on interpretation data associated with available medical imaging data. In some examples, a link to the one or more graphs may be included adjacent to a graphical representation of the pertinent medical characteristics. For example, a graph showing changes in stenosis within a carotid artery may be overlaid adjacent to a graphical representation of the stenosis at the particular point of interest within the carotid artery.

Further, the disclosure further describes techniques to search medical imaging data and corresponding interpretation data on a user interface of client device, based on a customizable and configurable set of search parameters. The search parameters may include, but are not limited to, an identification of an organ system, a medical specialty, a medical imaging techniques, a patient identifier, or a patient demographic data. Patient demographic data may include, but is not limited to, age, gender, or geographic location.

Further, the disclosure describes an anonymization component that may remove personally identifiable data from medical imaging data records for the purpose of generating an aggregated pool of data that may be searchable based on demographic, non-identifiable patient profile data and pertinent medical characteristics. The purpose of doing so is to provide medical research personnel and institutions with a data pool whereby medical condition trends and diagnoses may be identified based on shared characteristics shared between patients. Demographic and non-identifiable patient profile data may include, but is not limited to, patient geographic location, age, gender, ethnicity, and familial medical history. Further, pertinent medical characteristics may be based on interpretation data of medical imaging data. For example, interpretation data associated with a carotid artery may include pertinent medical characteristics, such as a percentage stenosis, plaque characteristics, and blood flow rate.

The term "techniques," as used herein, may refer to system(s), method(s), computer-readable instructions, module(s), algorithms, hardware logic, and/or operation(s) as permitted by the context described above and throughout the disclosure.

Figure 1:
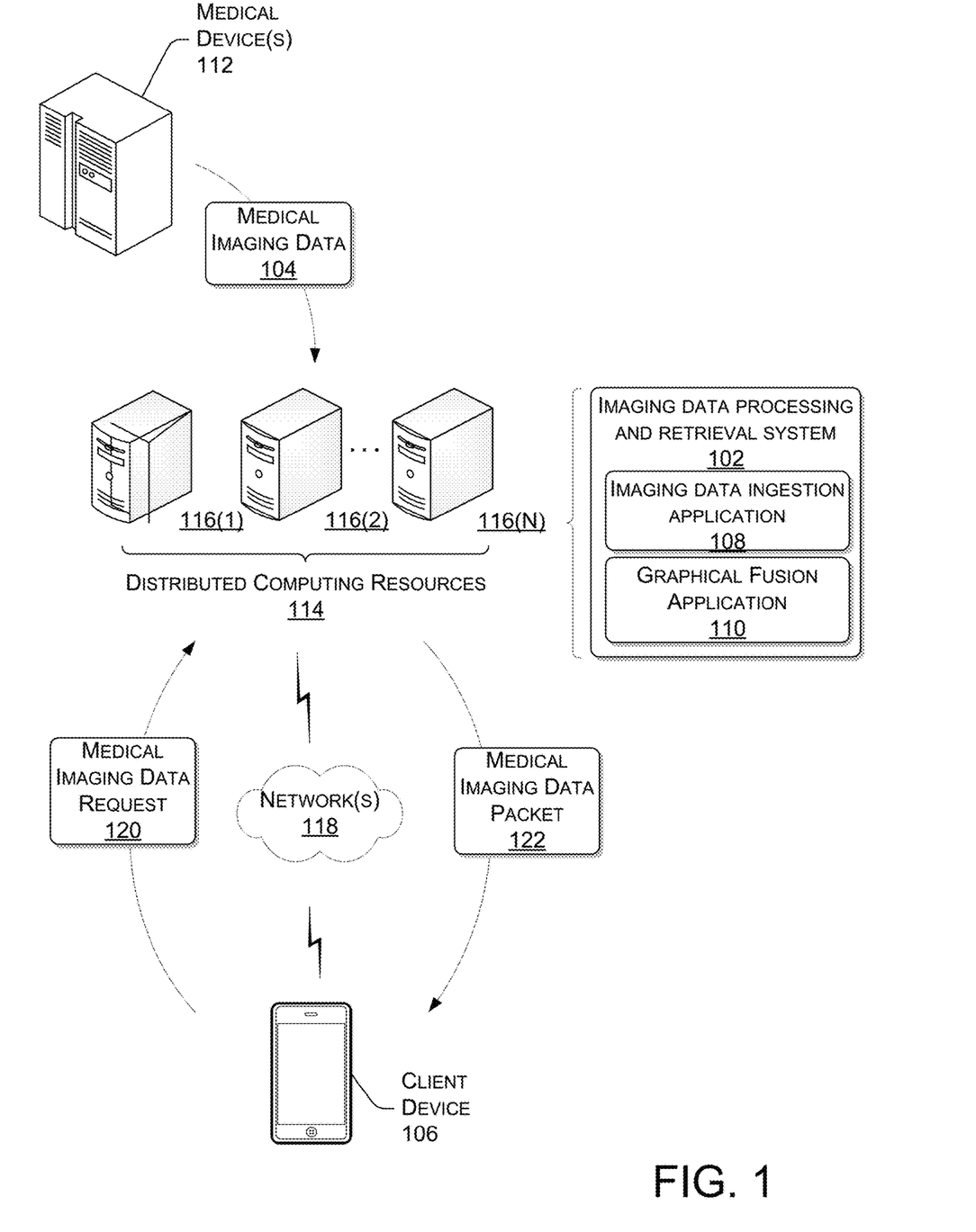
FIG. 1 illustrates a schematic view of an image data processing and retrieval system that analyses, aggregates and presents medical imaging data to a user interface of a client device.

FIG. 1 illustrates a schematic view of an image data processing and retrieval system 102 that analyses, aggregates and presents medical imaging data 104 to a user interface of a client device 106. The image data processing and retrieval system 102 may include an image data ingestion application 108 that analyses and aggregates medical imaging data, and a graphical fusion application 110 that facilitates a retrieval and presentation of medical imaging data 104 on a user interface of a client device 106. In some examples, the image data ingestion application 108 may generate interpretation data of medical imaging data that is based on an analysis of the medical imaging data. In this instance, an analysis of the medical imaging data may employ probabilistic machine learning analysis algorithms to interpret text and images of medical imaging data. Further, the image data ingestion application 108 may aggregate the medical imaging data and corresponding interpretation data based at least in part on one or more criteria including, patient identifier, organ system, medical specialty, or medical imaging device used to generate the medical imaging data. A benefit of doing so may allow medical practitioners to compile patient-specific medical data that may help facilitate intra-departmental and inter-departmental patient care. An additional benefit may be to facilitate medical practitioners in compiling medical data that is easily accessible on a population level for the purpose of researching and understanding different medical abnormalities and other disease processes across populations.

In various examples, the medical imaging data 104 and interpretation data may be stored within a data-store of the image data processing and retrieval system 102. The medical imaging data 104 and corresponding interpretation data may be associated with metadata that describe pertinent characteristics such as, but not limited to, a patient identifier, organ system identifier, medical specialty identifier, medical imaging technique identifier, examination identifier, and patient demographic identifiers.

In the illustrated example, the image data ingestion application 108 may receive medical imaging data 104 captured by one or more medical imaging device(s) 112. The medical imaging device(s) 112 may include, but are not limited to, x-ray, magnetic resonance imaging (MM), computed tomography (CT), ultrasound, and Positron Emission Tomography (PET). Further, the one or more medical imaging device(s) 112 may capture medical imaging data 104 that relates to one or more organ system(s) of a patient. The organ systems may include, but are not limited to, a cerebrovascular system, cardiovascular system, musculoskeletal system, pulmonary system, central nervous system, or gastrointestinal system.

In the illustrated example, the medical imaging device(s) 112 may be communicatively coupled to the to a medical imaging data processing and retrieval system 102 may include an image data ingestion application 108 and a graphical fusion application 110. The image data ingestion application 108 may receive, aggregate, and analyze medical imaging data 104 based at least in part on relevant medical examination criteria. For example, ultrasound, medical imaging data 104, may be associated with the cerebrovascular anatomy. The ultrasound may be analyzed to quantify stenosis, plaque characteristics, and blood flow velocity— namely, peak systolic velocity (PSV) and end diastolic velocity (EDV)—associated with corresponding arteries or veins. Similarly, medical imaging data 104 may correspond to an ultrasound of a carotid artery may be analyzed to quantify a set or similar set of criteria, namely, stenosis, plaque characteristics, PSV, and EDV. The image data ingestion application 108 may further include a data-store that stores an interpretation of the medical imaging data 104. The interpretation data may be based at least in part on an analysis of the medical imaging data 104 performed by the image data ingestion application 108. Further, medical imaging data 104 may be aggregated based on an organ system, medical specialty, or medical imaging device used to generate the medical imaging data 104. For example, medical imaging data 104 may be aggregated based on an organ system, including but not limited to, vascular system, musculoskeletal system, pulmonary system, central nervous system, or gastrointestinal system. Medical imaging data 104 may be further aggregated into focused examinations within each organ system. For example, medical imaging data 104 that relates to a vascular system may be further categorized into focused examination categories that include, but are not limited to, carotid, renal, vein, neurovascular, invasive peripheral, and dialysis access.

In the illustrated example, the graphical fusion application 110 may facilitate retrieval and presentation of the medical imaging data 104 and interpretation data on a user interface of a client device 106. The medical imaging data 104 and interpretation data may be based at least in part on a customizable set of search parameters. The set of search parameters may correspond to the metadata associated within the medical imaging data and corresponding interpretation data that is stored within the data-store. That is, the set of search parameters may include a patient identifier, one or more patient demographic identifier(s), an organ system identifier, a medical specialty identifier, a medical imaging technique identifier, and a result identifier. The result identifier may correspond to the type of interpretation data that is extracted from the medical imaging data. For example, result identifier associated with medical imaging data of a carotid artery may include a percentage of stenosis, plaque characteristics, or blood flow rate (i.e., peak systolic velocity and end diastolic velocity). Further, the one or more patient demographic identifiers may include non-identifiable patient information such as age, gender, ethnicity, geographical location, and familial medical history.

In a non-limiting example, the graphical fusion application 110 may receive a request to retrieve medical imaging data 104 and interpretation data based on a set of search parameters that include cerebrovascular anatomy (i.e., organ system) of a particular patient (i.e., patient identifier). In doing so, the graphical fusion application 110 may access the data-store associated with the image data processing and retrieval system 102 to retrieve the relevant medical imaging data and corresponding interpretation data. In another non-limiting example, the graphical fusion application 110 may receive a set of search parameters that relate to a population of male patients over a particular age (i.e., patient demographic identifier) with a minimum percentage of stenosis (i.e., medical examination result identifier) within the carotid artery (i.e., organ system). Further, the set of search parameters may indicate a user selection to anonymize identifiable patient information from medical imaging data 104 and corresponding interpretation data. In doing so, anonymized medical imaging data may be aggregated into a pool of data that may be searchable by demographic, non-identifiable patient profile information, characteristics of the medical imaging data 104, or a corresponding interpretation of such. A benefit of doing so may be to facilitate medical practitioners in compiling medical data that is easily accessible on a population level for the purpose of researching and understanding different medical abnormalities and other disease processes across populations.

In the illustrated example, the image data processing and retrieval system 102 may operate one or more distributed computing resource(s) 114. The distributed computing resource(s) 114 may include one or more computing device (s) 116 that are operate in a cluster or other configuration to share resources, balance load, increase performance, provide fail-over support or redundancy, or for other purposes.

In various examples, the one or more computing device(s) 116 may include one or more interfaces to enable communications with other networked devices, such as the client device 106, via one or more network(s) 118. For example, the one or more network(s) 118 may include public networks such as the Internet, private networks such as an institutional and/or personal intranet, or some combination of private and public networks. The one or more network(s) 118 can also include any type of wired and/or wireless network, including but not limited to local area network (LANs), wide area networks (WANs), satellite networks, cable networks, Wi-Fi networks, Wi-Max networks, mobile communications networks (e.g., 3G, 4G, and so forth), or any combination thereof.

In the illustrated example, the client device 106 may be communicatively coupled to the image data processing and retrieval system 102 via the one or more network(s) 118. In various examples, the client device 106 may transmit a medical imaging data request 120 to the image data processing and retrieval system 102. The medical image data request 120 may include a set of parameters the define the scope of the request. For example, the set of parameters may include, but are not limited to a patient identifier, one or more patient demographic identifier(s), an organ system identifier, a medical specialty identifier, a medical imaging technique identifier, or a result identifier. Further, in response to sending the medical image data request 120, the client device 106 may receive a medical imaging data packet 122 that is based at least in part on the set of parameters that were set out in the medical image data request 120. In various examples, the medical imaging data packet 122 may include medical imaging data 104 along with corresponding interpretation data. Interpretation data may correspond to pertinent medical characteristics that are deduced based on an analysis of the medical imaging data 104.

The client device 106 may include any sort of electronic device, such as a cellular phone, a smart phone, a tablet computer, an electronic reader, a media player, a gaming device, a personal computer (PC), a laptop computer, etc.

Figure 2:
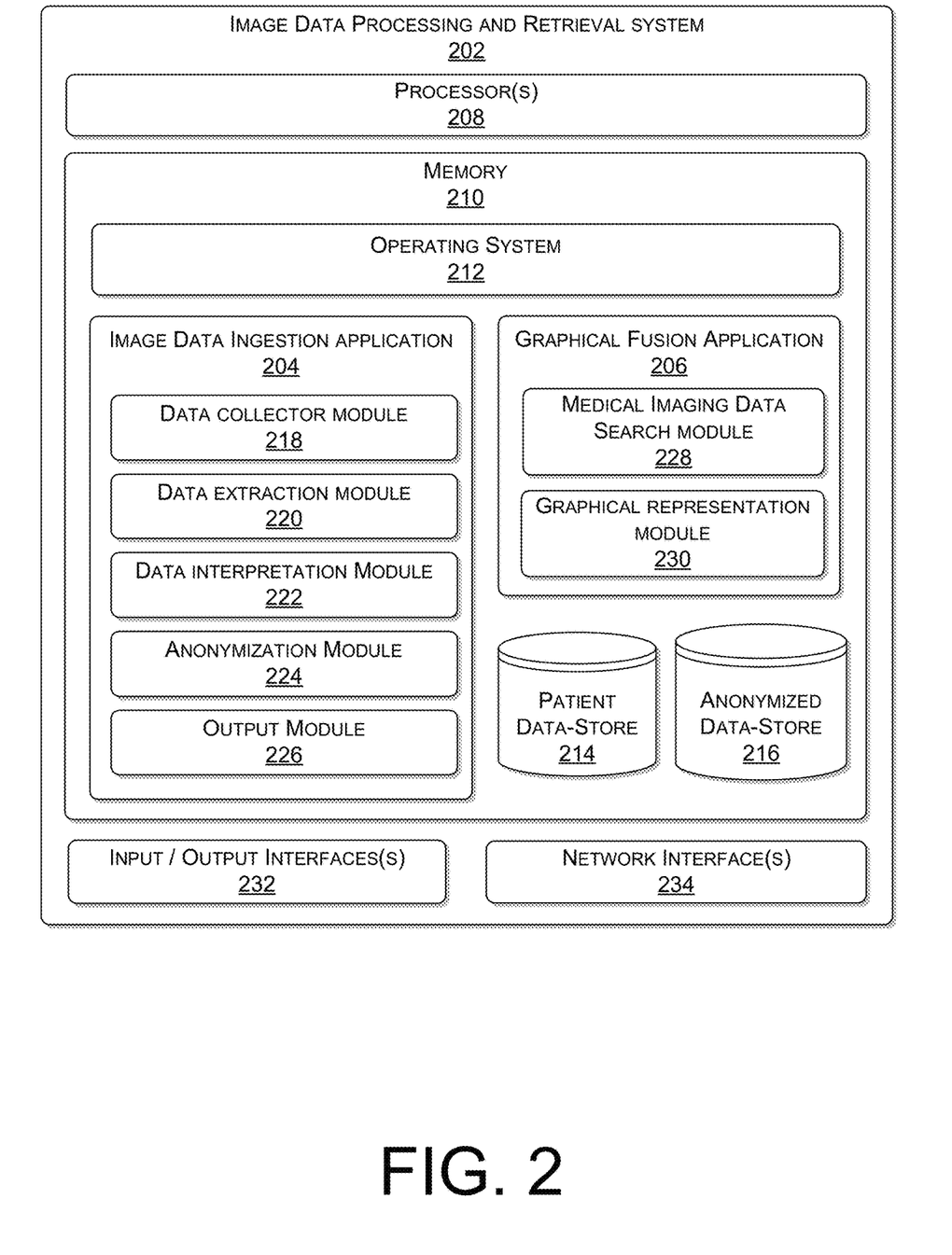
FIG. 2 illustrates a block diagram of the image data processing and retrieval system that analyses and aggregates medical imaging data, and further facilitates the retrieval and presentation of the medical imaging data and corresponding interpretation data.

FIG. 2 illustrates a block diagram of the image data processing and retrieval system 202 that analyses and aggregates medical imaging data, and further facilitates the retrieval and presentation of the medical imaging data and corresponding interpretation data, based at least in part on a set of customizable and configurable search parameters. In the illustrated example, the image data processing and retrieval system 202 may correspond to the image data processing and retrieval system 102. Further, the image data processing and retrieval system 202 may include an image data ingestion application 204 and a graphical fusion application 206.

In the illustrated example, the image data ingestion application 204 and the graphical fusion application 206 may correspond to image data ingestion application 108 and the graphic fusion application 110 respectively. Further, the image data processing and retrieval system 202 may include one or more processor(s) 208 that are operably connected to memory 210. In at least one example, the one or more processor(s) 208 may be one or more central processing unit(s) (CPU), graphics processing unit(s) (GPU), both a CPU and GPU, or any other sort of processing unit(s). Each of the one or more processor(s) 208 may have numerous arithmetic logic units (ALUs) that perform arithmetic and logical operations as well as one or more control units (CUs) that extract instructions and stored content from processor cache memory, and then executes these instructions by calling on the ALUs, as necessary during program execution. The one or more processor(s) 208 may also be responsible for executing all computer applications stored in the memory, which can be associated with common types of volatile (RAM) and/or nonvolatile (ROM) memory.

In some examples, memory 210 may include system memory, which may be volatile (such as RAM), non-volatile (such as ROM, flash memory, etc.) or some combination of the two. The memory may also include additional data storage devices (removable ad/or non-removable) such as, for example, magnetic disks, optical disks, or tape.

The memory 210 may further include non-transitory computer-readable media, such as volatile and nonvolatile, removable and non-removable media implemented in any method or technology for storage of information, such as computer readable instructions, data structures, program modules, or other data. System memory, removable storage and non-removable storage are all examples of non-transitory computer-readable media. Examples of non-transitory computer-readable media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information.

In the illustrated example, the memory 210 may include an operating system 212, the image data ingestion application 204, the graphical fusion application 206, a patient data-store 214, and an anonymized data-store 216. The operating system 212 may be any operating system capable of managing computer hardware and software resources.

In the illustrated example, the image data ingestion application 204 may further include a data collector module 218, a data extraction module 220, a data interpretation module 222, an anonymization module 224, and an output module 226. The data collector module 218 may receive medical imaging data 104 from one or more medical imaging device(s) 112. The medical imaging data 104 may comprise of medical images associated with a particular medical examination performed by a medical imaging device. In some examples, the medical imaging data may relate to one or more organ system(s) of a particular patient, such as but not limited to, cerebrovascular system, cardiovascular system, musculoskeletal system, pulmonary system, central nervous system, or gastrointestinal system. Further, the medical imaging device(s) may include, but are not limited to, x-ray, magnetic resonance imaging (MRI), computed tomography (CT), ultrasound, and Positron Emission Tomography (PET).

The data extraction module 220 may employ object recognition algorithms to extract pertinent medical characteristics from the medical imaging data 104. Pertinent medical characteristics may vary based on the medical imaging data and the associated organ system. For example, pertinent medical characteristics associated with the vascular system may include, but are not limited to, percentage of stenosis, blood flow velocity (i.e., peak systolic velocity (PSV) and an end diastolic velocity (EDV)), and plaque characteristics. The object recognition algorithms may employ optical character recognition (OCR) algorithms to extract text data from the medical imaging data 104. Text data may include a patient identifier, a medical imaging technique identifier, an organ system identifier, and a date and time of when the medical imaging data was captured. In some examples, the medical imaging data may also include text that describes some results associated with the medical imaging data. For example, an ultrasound of a particular vascular system may include a measured PSV and EDV.

Object recognition algorithms may employ appearance-based and feature-based methods to help identify pertinent medical characteristics associated with medical imaging data 104. Appearance-based methods may identify a graphical representation (i.e., non-text image data) of medical data based on a comparison with template images. Template images may correspond to patient-specific template images from prior medical examinations. Alternatively, or additionally, template images may correspond to medical images from a population of patients. Feature-based methods may extract features from objects, such as surface patches, corners, and linear edges, as a means of identifying the underlying object. Feature-based methods may be useful in recognizing changes in shape and size of objects. Particularly, feature-based methods may be useful in deducing medical characteristics from a medical image, such as a percentage of stenosis within a particular blood vessel.

In various examples, the data interpretation module 222 may further analyze the medical imaging data 104 to quantify one or more medical characteristics associated with the medical imaging data. The data interpretation module 222 may employ probabilistic machine learning analysis algorithms to analyze the medical imaging data 104. The analysis of medical imaging data 104 may include an analysis of images captured by the medical imaging device(s) 112 as well as images of graph-data that represent pertinent medical characteristics captured by the medical imaging data 104. For example, graph data associated data may correspond to changes in blood flow velocity between PSV and ESV. In this instance, the data interpretation module 222 may analyses the graph data to quantify a PSV and ESV. In another example, the medical imaging data may be associated with electrocardiography (ECG), a process of recording electrical activity of the heart over a period of time using electrodes on the skin. The data interpretation module 222 may interpret the ECG to determine the presence and prominence of four entities in a normal rhythm, those being atrial depolarization, ventricular depolarization, ventricular repolarization, and papillary muscle repolarization.

In another example, images within medical imaging data 104 may present a color tone or change in contour of an anatomical feature (i.e., stenosis of a blood vessel). The color tone or change in contour may be intended to reflect pertinent medical characteristics of the anatomy, such as a percentage of stenosis within a blood vessel, characteristics of plaque buildup on the walls of the blood vessel, or the blood flow velocity (i.e., peak systolic velocity or end diastolic velocity) through the blood vessel. Probabilistic machine learning analysis algorithms, along with reference template medical imaging data, may help interpret a meaning associated with the image features. The reference template medical imaging data may be based at least in part on a reference database within the patient data-store 214 of the medical imaging data processing and retrieval system 202. Alternatively, or additionally, the reference template medical imaging data may be based at least in part on patient-specific template images from prior medical examinations, or cumulative template medical images from a population of patients.

In various examples, the data interpretation module 222 may generate interpretation data that is associated with the analysis of the medical imaging data 104. The interpretation data may collate the analysis of text data and image data associated with the medical imaging data 104, along with a determination of pertinent medical characteristics (i.e., PSV, ESV, percentage stenosis, plaque buildup characteristics, heart rhythm, etc.). The interpretation data may be associated with the medical imaging data 104 within the patient data-store 214.

The data interpretation module 222 may aggregate and associate the medical imaging data 104 and corresponding interpretation data with an appropriate database record of the patient data-store 214. In some examples, the appropriate database record may correspond to a patient-specific record entry. Alternatively, or additionally, the appropriate database record may correspond to pertinent medical characteristics or text data extracted from the medical imaging data 104. For example, database records may be arranged based on a medical imaging technique identifier, or an organ system identifier, or a patient demographic identifier. Note that selection of the database record may be based at least in part on the interpretation data associated with the medical imaging data 104.

The anonymization module 224 may remove personally identifiable data from medical imaging data 104 stored within the patient data-store 214 for the purpose of generating an aggregated pool of data that may be searchable based on demographic, non-identifiable patient profile data and pertinent medical characteristics. The purpose of doing so is to provide medical research personnel and institutions with a data pool whereby medical condition trends and diagnoses may be identified based on shared characteristics shared between patients. Demographic and non-identifiable patient profile data may include, but is not limited to, patient geographic location, age, gender, ethnicity, and familial medical history. Pertinent medical characteristics may be based on interpretation data of medical imaging data. For example, interpretation data associated with a carotid artery may include pertinent medical characteristics, such as a percentage stenosis, plaque characteristics, and blood flow rate. In some examples, the anonymized data records may be stored within a separate anonymized data-store 216 of the image data processing and retrieval system 202. Further, anonymized database record entries may be arranged based on a medical imaging technique identifier, or an organ system identifier, or a patient demographic identifier.

The output module 226 may transmit the medical imaging data 104 and interpretation data to one of the patient data-store 214 or the anonymized data-store 216. For example, medical imaging data 104 and interpretation data that includes with identifiable patient profile data may be transmitted to the patient data-store 214. Alternatively, medical imaging data 104 and interpretation data that has had personally identifiable data removed via the anonymization module 224, may be transmitted to the anonymized data-store 216.

In the illustrated example, the graphical fusion application 206 may facilitate a retrieval and presentation of the medical imaging data 104 and interpretation data on a user interface of a client device 106. In the illustrated example, the graphical fusion application 206 may include a medical imaging data search module 228, and a graphical representation module 230. The medical imaging data search module 228 may retrieve medical imaging data 104 and corresponding interpretation data from one of the patient data-store 214, or the anonymized data-store 216. Further, the retrieval of medical imaging data and corresponding interpretation data may be based at least in part on a set of customizable and configurable parameters. The set of parameters may include, but are not limited to, an organ system identifier, a medical specialty identifier, medical imaging techniques, patient identifier, or patient demographic identifiers. In various examples, the set of parameters may be included with a request for medical imaging data and corresponding interpretation data. In some examples, a search may be further based on medical results associated with the medical imaging data. In this instance, the set of parameters may also include a medical result identifier that pertains to pertinent medical characteristics. In a non-limiting example, the graphical fusion application 206 may receive a request for retrieval and presentation of medical imaging data 104 and interpretation data that relates to males within a particular geographical locale that have exhibited stenosis of fifty percent or greater within one an artery of the cerebrovascular anatomy. In this example, stenosis of fifty percent or greater may be considered the medical result identifier, since stenosis may be a pertinent medical characteristic of medical imaging data.

The graphical representation module 230 may graphically display pertinent medical characteristics on a schematic diagram of an organ system. Pertinent medical characteristics may include stenosis, blood flow velocity (i.e., PSV and ESV), or plaque characteristics. For example, consider an ultrasound test that is performed on a carotid artery, for the purpose of ascertaining a level of stenosis at the artery walls.

In this example, the pertinent medical characteristic corresponds to the stenosis at the artery walls, and the organ system corresponds to the carotid artery. Thus, in this example, medical imaging data and corresponding interpretation data may be used to graphically represent the stenosis at the artery walls as a constriction of artery. The constriction may be graphically overlaid onto a schematic diagram of the carotid artery, and further positioned at a location on the schematic diagram that is closely aligned with the medical test location. In doing so, the graphical representation module 230 may graphically illustrate the presence and location, of the stenosis within the carotid artery.

In various examples, the graphical representation module 230 may further provide a link to relevant medical imaging data adjacent to the graphical representation of the constriction (i.e., stenosis). In some examples, the graphical fusion application may retrieve a temporal sequence of medical imaging data that show changes in a pertinent medical characteristic, such as the percentage of stenosis within the carotid artery, over a predetermined period of time.

Further, the graphical representation module 230 may generate a graph that represents changes in pertinent medical characteristics over a predetermined period of time. For example, changes in blood flow velocity (i.e., PSV or ESV), or stenosis may be graphed over a predetermined period of time, based on the availability of the relevant medical imaging data across the predetermined period of time. The graphical representation module 230 may generate one or more graphs based on interpretation data associated with the available medical imaging data. In some examples, a link to the one or more graphs may be included adjacent to a graphical representation of the pertinent medical characteristics. For example, a graph showing changes in stenosis within a carotid artery may be overlaid adjacent to a graphical representation of the stenosis at the particular point of interest within the carotid artery.

In the illustrated example, the image data processing and retrieval system 202 may further include input/output interface(s) 232. The input/output interface(s) 232 may include any type of output interface known in the art, such as a display (e.g., a liquid crystal display), speakers, a vibrating mechanism, or a tactile feedback mechanism. Input/output interface(s) 232 also include ports for one or more peripheral devices, such as headphones, peripheral speakers, or a peripheral display. Further, the input/output interface(s) 232 may further include a camera, a microphone, a keyboard/keypad, or a touch-sensitive display. A keyboard/keypad may be a push button numerical dialing pad (such as on a typical telecommunication device), a multi-key keyboard (such as a conventional QWERTY keyboard), or one or more other types of keys or buttons, and may also include a joystick-like controller and/or designated navigation buttons, or the like.

In the illustrated example, the image data processing and retrieval system 202 may include one or more network interface(s) 234. The one or more network interface(s) 234 may include any sort of transceiver known in the art. For example, the one or more network interface(s) 234 may include a radio transceiver that performs the function of transmitting and receiving radio frequency communications via an antenna. In addition, the one or more network interface(s) 234 may also include a wireless communication transceiver and a near field antenna for communicating over unlicensed wireless Internet Protocol (IP) networks, such as local wireless data networks and personal area networks (e.g., Bluetooth or near field communication (NFC) networks). Further, the one or more network interface(s) 234 may include wired communication components, such as an Ethernet port or a Universal Serial Bus (USB).

Figure 3:
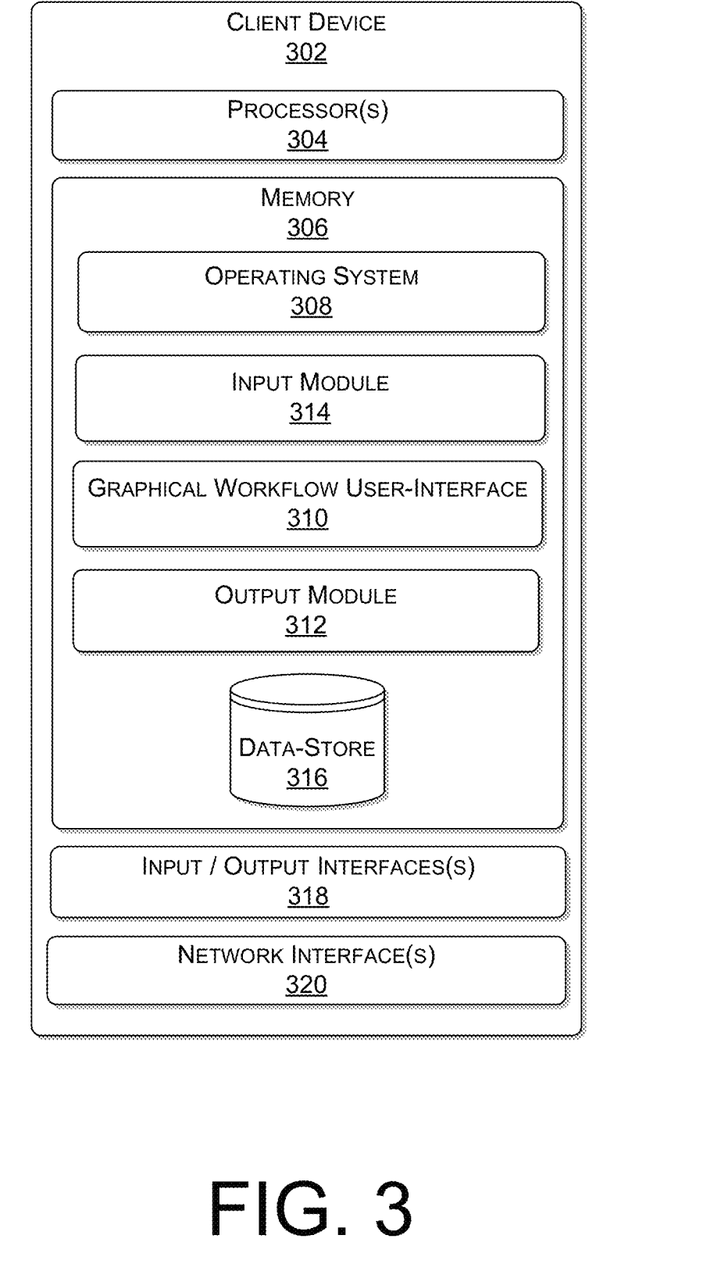
FIG. 3 illustrates a block diagram of a client device that may interface with the image data processing and retrieval system.

FIG. 3 illustrates a block diagram of a client device 302 that may interface with the image data processing and retrieval system 202. In various examples, the client device 302 may request and receive medical imaging data and corresponding interpretation data that is associated with a particular patient, or a population of patients. In the illustrated example, the client device 302 may correspond to client device 302. Further, the client device 302 may include one or more processor(s) 304 operably connected to memory 306. The one or more processor(s) 304 may correspond to the one or more processor(s) 208, and the memory 306 may correspond to the memory 210.

In the illustrated example, the memory 306 may include an operating system 308, a graphical workflow user-interface 310, and an output module 312. The operating system 308 may be used to implement the graphical workflow user-interface 310. The operating system 308 may be any operating system capable of managing computer hardware and software resources. The graphical workflow user-interface 310 may include routines, program instruction, objects, and/or data structures that perform particular tasks or implement particular abstract data types.

The graphical workflow user-interface 310 may facilitate user input of a set of parameters to request and receive a presentation of medical imaging data and corresponding interpretation data. In various examples, the client device 302 may interact with the graphical fusion application 206 of the image data processing and retrieval system 202, and thus receive a graphical presentation of pertinent medical characteristics on a schematic diagram of an organ system. For example, the client device 302 may request results for an ultrasound medical test of a particular patient that performed on a carotid artery. In response, the graphical fusion application 206 may generate, and the client device 302 may receive, a graphical representation of stenosis as a constriction at the wall of the carotid artery. The constriction may be graphically overlaid onto a schematic diagram of the carotid artery, and further positioned at a location on the schematic diagram that is closely aligned with medical test location.

Further, the graphical workflow user-interface 310 may facilitate user input of a set of parameters to search and retrieve medical imaging data and corresponding interpretation data from a population of patients. A benefit of doing so may allow medical practitioners to compile medical data that is easily accessible on a population level for the purpose of researching and understanding different medical abnormalities and other disease processes across populations. Alternatively, the client device 302 may search and retrieve medical imaging data and corresponding interpretation data that is associated with a particular patient. A benefit of doing so may allow medical practitioners to compile patient-specific medical data that may help facilitate intra-departmental and inter-departmental patient care.

In other examples, the graphical workflow user-interface 310 may facilitate user input of a set of parameters to search and retrieve medical imaging data and corresponding interpretation data from a population of patients. A benefit of doing so may allow medical practitioners to compile medical data of a population of patients for the purpose of researching and understanding different medical abnormalities and other disease processes across populations. Alternatively, the client device 302 may search and retrieve medical imaging data and corresponding interpretation data that is associated with a particular patient. A benefit of doing so may allow medical practitioners to compile patient-specific medical data that may help facilitate intra-departmental and inter-departmental patient care.

The output module 312 may transmit a search request that is established via the graphical workflow user-interface. The search request may be transmitted to the graphical fusion application 206 for further processing. In some examples, the search request may be based at least in part on a set of customizable and configurable parameters. The set of parameters may include, but are not limited to, an organ system identifier, a medical specialty identifier, medical imaging techniques, patient identifier, or patient demographic identifiers. Further, the search request may also include a medical result identifier. For example, a search request may consider a patient population with a percentage of stenosis that is greater than fifty percent, and thus the search request would include the percentage of stenosis as a medical result identifier.

The input module 314 may receive medical imaging data and corresponding interpretation data that is based at least in part on a search request via the graphical workflow user-interface 310. In some examples, the medical imaging data and corresponding interpretation data may be associated with a specific patient, or a population of patients.

The data-store 316 may store medical imaging data and corresponding interpretation data that is received via the graphical workflow user-interface, and ultimately the input module 314. Further, the data-store 316 may store a record of search strings used to search for, and retrieve, medical imaging data and corresponding interpretation data.

In the illustrated example, the client device 302 may include input/output interface(s) 318 and network interfaces(s) 320. The input/output interface(s) 318 and the network interface(s) 320 may correspond to the input/output interface(s) 232 and the network interface(s) 234 respectively.

Figure 4A:
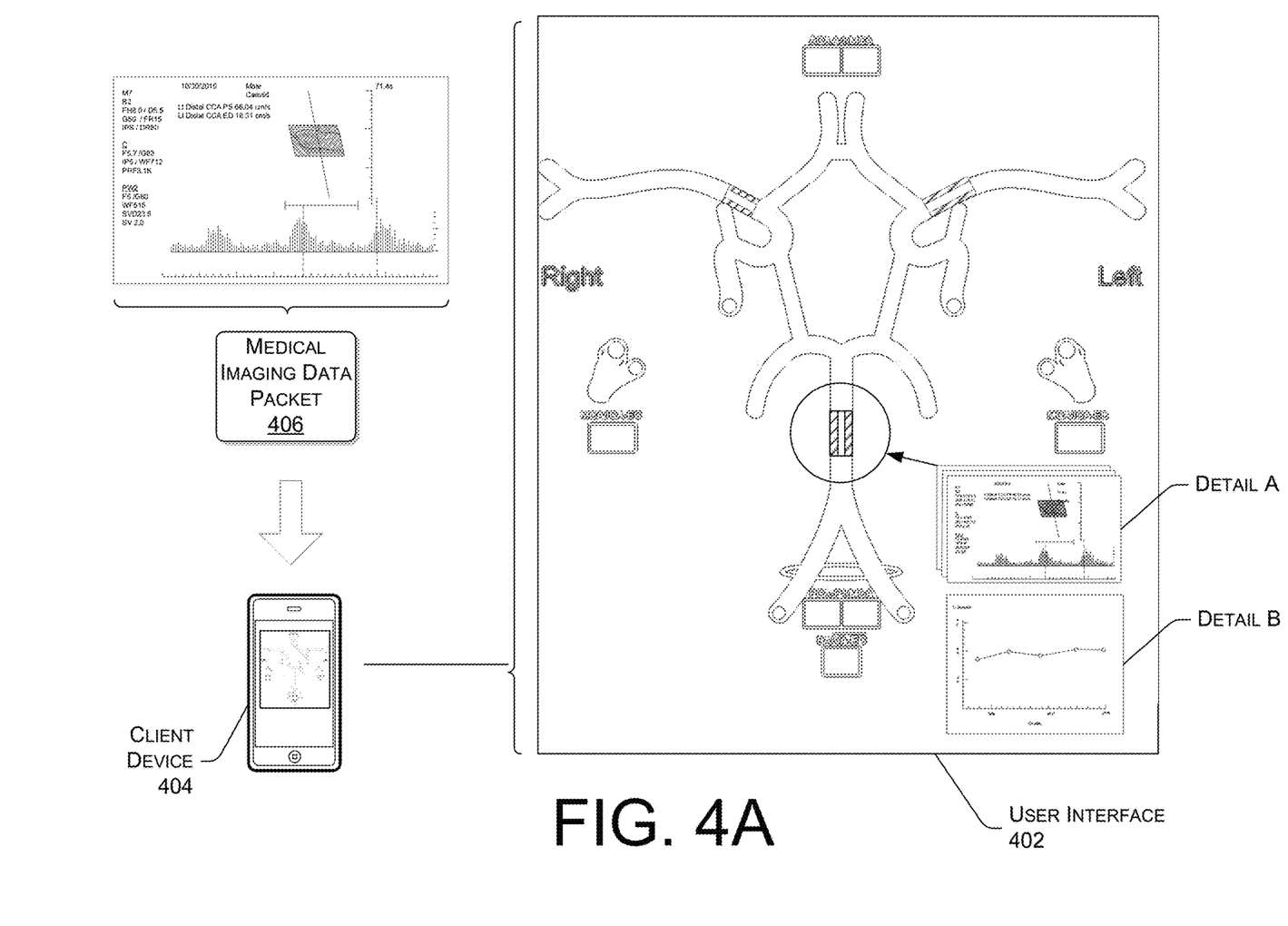
FIG. 4A illustrates a user interface 402 that may be presented on client device 404, in response to the client device 404 receiving a medical imaging data packet 406.

FIG. 4A illustrates a user interface 402 that may be presented on client device 404, in response to the client device 404 receiving a medical imaging data packet 406. In various examples, the medical imaging data packet 406 may include medical imaging data 104 along with corresponding interpretation data.

FIG. 4A further illustrates a graphical representation of pertinent medical characteristics on a schematic diagram of an organ system. Pertinent medical characteristics may include stenosis, blood flow velocity (i.e., PSV and ESV), or plaque characteristics. The illustrated example considers an ultrasound test that is performed on a carotid artery, for the purpose of ascertaining a level of stenosis at the artery walls. In this example, the pertinent medical characteristic corresponds to the stenosis at the artery walls, and the organ system corresponds to the carotid artery. Thus, in this example, medical imaging data and corresponding interpretation data may be used to graphically represent the stenosis at the artery walls as a constriction of artery. The constriction may be graphically overlaid onto a schematic diagram of the carotid artery, and further positioned at a location on the schematic diagram that is closely aligned with the medical test location. In doing so, the user interface 402 may graphically display the presence and location, of the stenosis within the carotid artery.

Figure 4B:
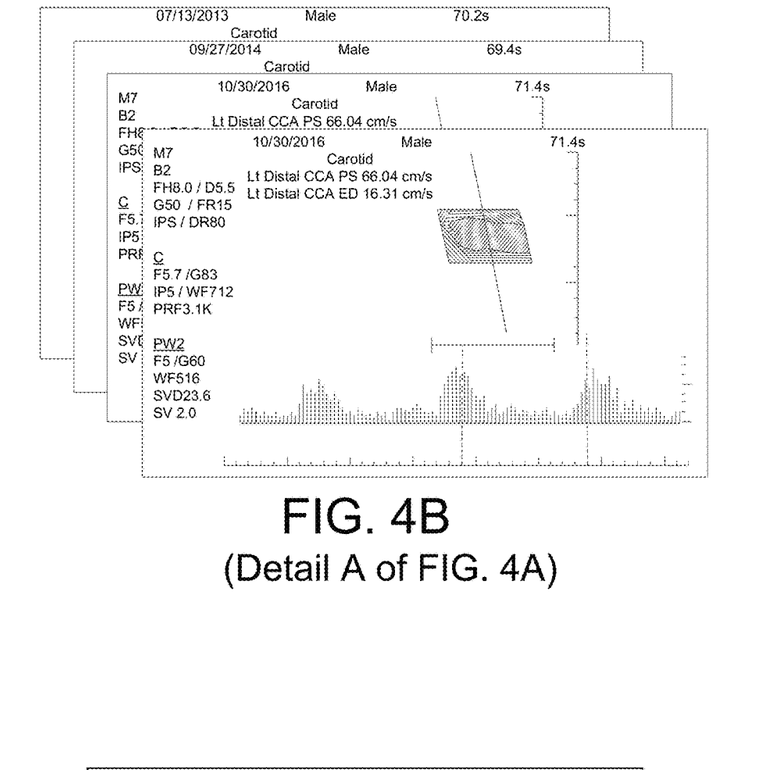
FIG. 4B further illustrates a link to relevant medical imaging data.

FIG. 4B further illustrates a link to relevant medical imaging data that is adjacent to the graphical representation. In this example, the relevant medical imaging data is adjacent to a constriction (i.e., stenosis), as shown as Detail A of FIG. 4A. In some examples, the graphical fusion application may retrieve a temporal sequence of medical imaging data that show changes in a pertinent medical characteristic, such as the percentage of stenosis within the carotid artery, over a predetermined period of time.

Figure 4C:
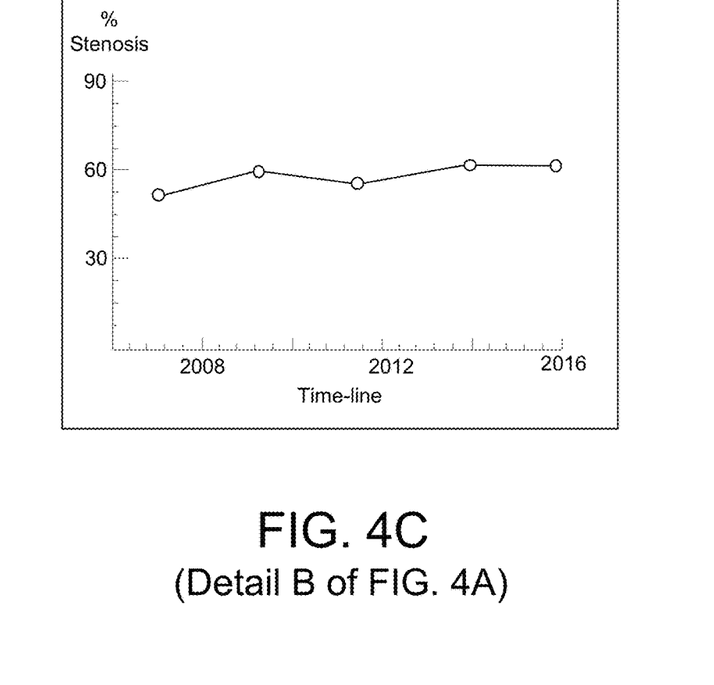
FIG. 4C further illustrates a graph that represents changes in pertinent medical characteristics over a predetermined period of time.

FIG. 4C further illustrates a graph that represents changes in pertinent medical characteristics over a predetermined period of time, as shown in Detail B of FIG. 4C. For example, changes in blood flow velocity (i.e., PSV or ESV), or stenosis may be graphed over a predetermined period of time, based on the availability of the relevant medical imaging data across the predetermined period of time. The user interface 402 of the client device 404 may display one or more graphs that are based on interpretation data associated with the available medical imaging data. In some examples, a link to the one or more graphs may be included adjacent to a graphical representation of the pertinent medical characteristics. For example, a graph showing changes in stenosis within a carotid artery may be overlaid adjacent to a graphical representation of the stenosis at the particular point of interest within the carotid artery.

Figure 5:
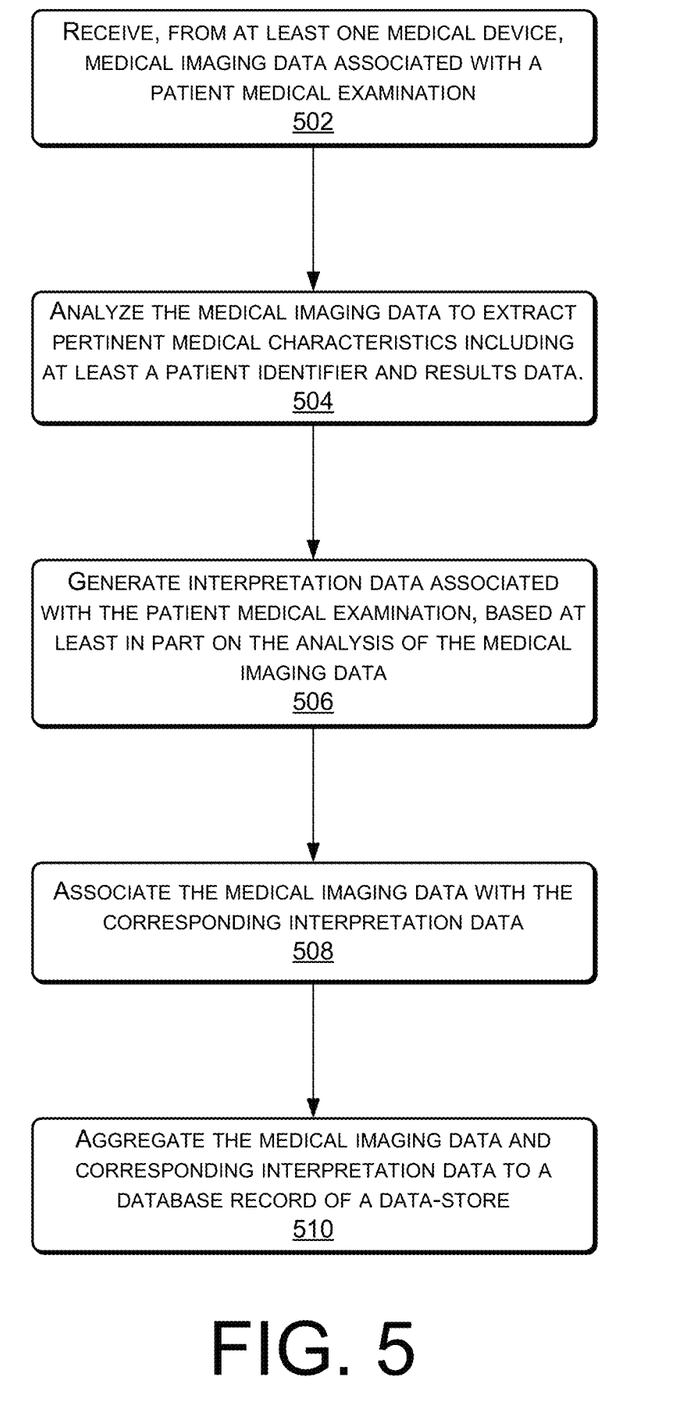
FIG. 5 illustrates a flow diagram of an image data ingestion application that receives medical imaging data associated with a patient medical examination.
Figure 6:
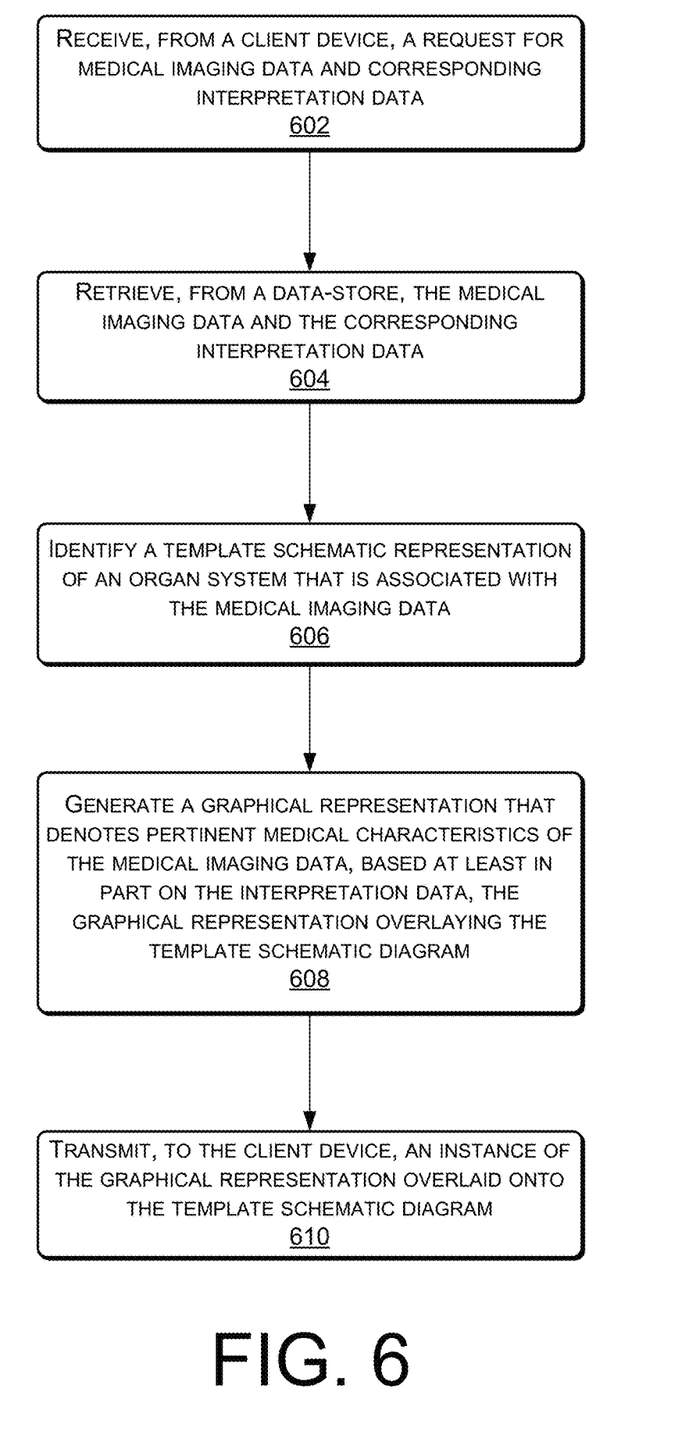
FIG. 6 illustrates a flow diagram of a graphical fusion application that receives and processes a request for medical imaging data and corresponding interpretation data.
Figure 7:
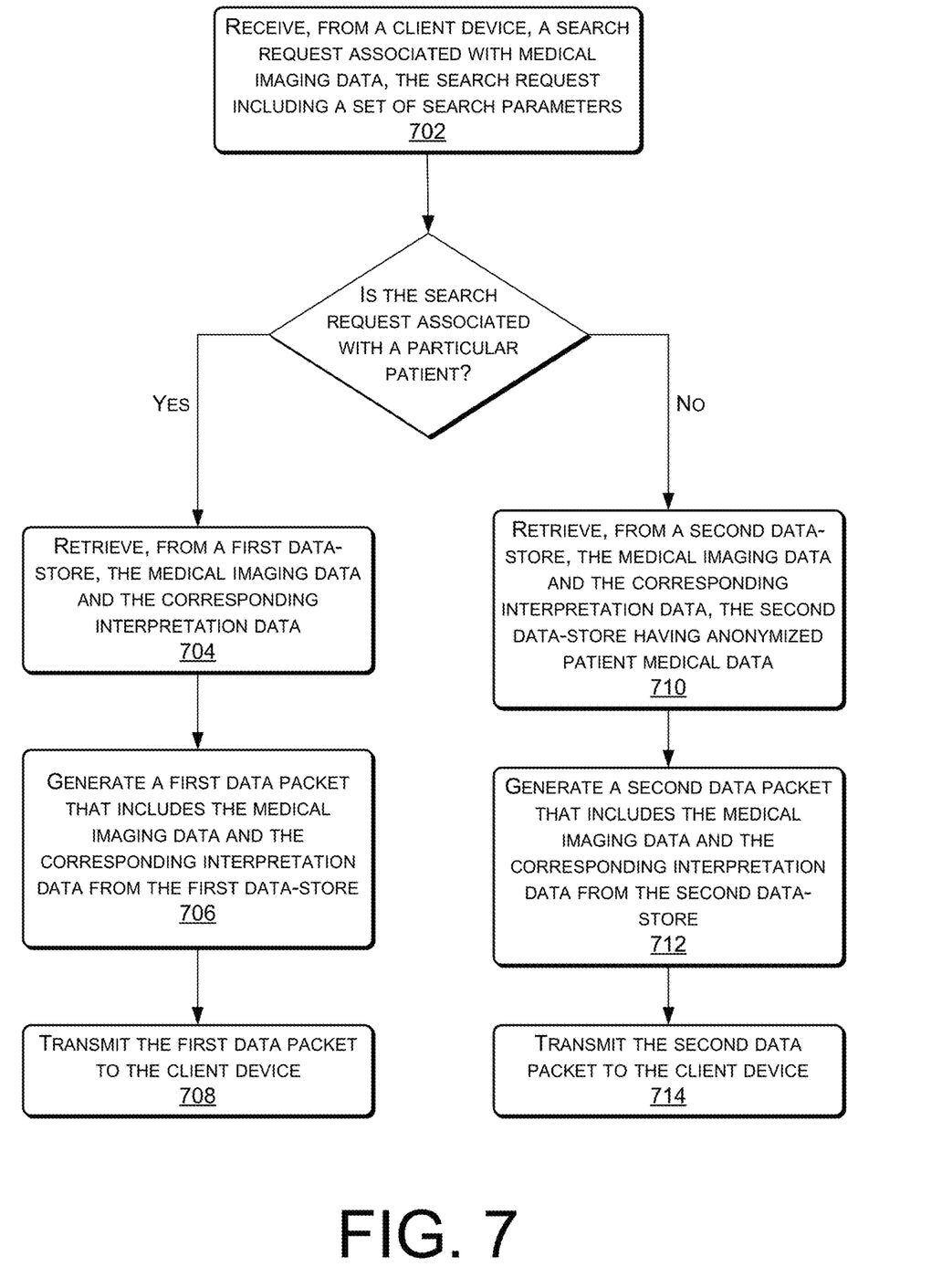
FIG. 7 illustrates a flow diagram of a client device that submits a search request for medical imaging data, based at least in part on one or more search parameters.

FIGS. 5, 6, and 7 present processes 500, 600, and 700 that relate to operations of the image data processing and retrieval system. Each of processes 500, 600, and 700 illustrate a collection of blocks in a logical flow chart, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes 500, 600, and 700 are described with reference to the computing environment 100 of FIG. 1.

FIG. 5 illustrates a flow diagram of an image data ingestion application that receives medical imaging data associated with a patient medical examination. The medical imaging data may relate to image data that is generated by medical imaging devices such as, but not limited to, x-ray, magnetic resonance imaging (MM), computed tomography (CT), ultrasound, and Positron Emission Tomography (PET).

At 502, the image data ingestion application may receive, from at least one medical device, medical imaging data associated with a patient medical examination. The patient medical examination may be associated with an organ system that includes, but is not limited to, a cerebrovascular system, cardiovascular system, musculoskeletal system, pulmonary system, central nervous system, or gastrointestinal system.

At 504, the image data ingestion application may analyze the medical imaging data to extract pertinent medical characteristics, including at least a patient identifier and medical results data. In various examples, an analysis of the medical imaging data may involve employing object recognition algorithms. Object recognition algorithms may further use optical character recognition, in addition to appearance-based and feature-based methods to help identify pertinent medical characteristics from the text and images of the medical imaging data.

At 506, the image data ingestion application may generate interpretation data associated with the patient medical examination, based at least in part on the analysis of the medical imaging data. The interpretation data may quantify pertinent medical characteristics from the medical imaging data, such as the blood flow velocity (i.e., PSV and ESV) and percentage stenosis of a blood vessel.

At 508, the image data ingestion application may associate the medical imaging data with the corresponding interpretation data. At 510, the image data ingestion application may aggregate the medical imaging data and the corresponding interpretation data based at least in part on one or more criteria including, but not limited to, patient identifier, organ system, medical specialty, or medical imaging device used to generate the medical imaging data. Further, the aggregated medical imaging data and interpretation data may be stored in a patient data-store for the purpose of allowing medical practitioners to compile patient-specific medical data that may help facilitate intra-departmental and inter-departmental patient care. Alternatively, or additionally, patient identifiable information may be removed from the aggregated medical imaging data and interpretation data for the purpose of compiling non-identifiable patient medical data of a population of patients for the purpose of researching and understanding different medical abnormalities and other disease processes across populations.

FIG. 6 illustrates a flow diagram of a graphical fusion application that receives and processes a request for medical imaging data and corresponding interpretation data. In some examples, the search request may be based at least in part on a set of customizable and configurable parameters. The set of parameters may include, but are not limited to, an organ system identifier, a medical specialty identifier, medical imaging techniques, patient identifier, or patient demographic identifiers.

At 602, the graphical fusion application may receive, from a client device, a search request for medical imaging data and corresponding interpretation data. In some examples, the search request may include a medical result identifier. For example, a search request may consider a patient population with a percentage of stenosis that is greater than fifty percent, and thus the search request would include the percentage of stenosis as a medical result identifier.

At 604, the graphical fusion application may retrieve, from a data-store, the medical imaging data and the corresponding interpretation data. In various examples, the graphical fusion application may access a patient data-store or an anonymized data-store. A patient data-store may include patient-specific medial data for the purpose of allowing medical practitioners to help facilitate intra-departmental and inter-departmental patient care. Alternatively, or additionally, an anonymized data-store may have patient identifiable information removed, whereby medical practitioners are interested in compiling medical data of a population of patients for the purpose of researching and understanding different medical abnormalities and other disease processes across populations.

At 606, the graphical fusion application may identify a template schematic diagram of an organ system that is associated with the medical imaging data. Template images may correspond to patient-specific template images from prior medical examinations. Alternatively, or additionally, template images may correspond to medical images from a population of patients.

At 608, the graphical fusion application may generate a graphical representation that denotes pertinent medical characteristics of the medical imaging data, based at least in part on the interpretation data, the graphical representation overlaying the template schematic diagram.

At 610, the graphical fusion application may transmit to the client device, an instance of the graphical representation overlaid onto the template schematic diagram. For example, medical imaging data associated with a cerebrovascular system of a particular patient may be analyzed to quantify a percentage of stenosis due to plaque buildup at a particular point along the carotid artery. The stenosis may be graphically represented as a constriction of the carotid artery. The graphical representation of the constriction may overlay the schematic diagram of the carotid artery.

FIG. 7 illustrates a flow diagram that describes a graphical fusion application that receives, from a client device, a search request for medical imaging data, based at least in part on one or more search parameters.

At 702, the graphical fusion application may receive, from a client device, a search request associated with medical imaging data, the search request including a set of search parameters. In various examples, the search parameters may include, but are not limited to, an identification of an organ system, a medical specialty, a medical imaging techniques, a patient identifier, or a patient demographic data. Patient demographic data may include, but is not limited to, age, gender, or geographic location.

At 704, the graphical fusion application may determine that the search request is associated with a particular patient, rather than a population of patients. In various examples, the search request may include a patient identifier as a means of determining that the search request is associated with a particular patient. Thus, the graphical fusion application may retrieve, from a first data-store, medical imaging data and corresponding interpretation data that corresponds to the patient. The first data-store may correspond to a patient data-store.

At 706, the graphical fusion application may generate a first data packet that includes the medical imaging data and the corresponding interpretation data. In various examples, the interpretation data may quantify pertinent medical characteristics from the medical imaging data, such as the blood flow velocity (i.e., PSV and ESV) and percentage stenosis of a blood vessel.

At 708, the graphical fusion application may transmit the first data packet to the client device for display via a user-interface. In various examples, the client device may include a graphical workflow user interface that facilitates the display of second data packet.

At 710, the graphical fusion application may determine that the search request is associated with a population of patients, rather than a specific patient. A benefit of performing such a search request may be to facilitate researching and understanding different medical abnormalities and other disease processes across populations. In doing so, the graphical fusion application may retrieve, from a second data-store, medical imaging data and corresponding interpretation data, the second data-store having anonymized patient medical data. Anonymized patient medical data may be generated by removing personally identifiable data from medical imaging data records.

At 712, the graphical fusion workflow application may generate a second data packet that includes the medical imaging data and the corresponding interpretation data. Absent personally-identifiable information, the medical imaging data may include, but is not limited to, patient geographic location, age, gender, ethnicity, and familial medical history. Further, the interpretation data may include pertinent medical characteristics that are based at least in part on an analysis of the medical imaging data. For example, interpretation data associated with a carotid artery may include pertinent medical characteristics, such as a percentage stenosis, plaque characteristics, and blood flow rate. In other words, pertinent medical characteristics, such as a percentage stenosis, plaque characteristics, and blood flow rate may be deduced by analysis of medical imaging data.

At 714, the graphical fusion workflow application may transmit the second data packet to the client device for display via the user interface. In various examples, the client device may include a graphical workflow user interface that facilitates the display of second data packet.

CONCLUSION

Although the subject matter has been described in language specific to features and methodological acts, it is to be understood that the subject matter defined in the appended claims is not necessarily limited to the specific features or acts described herein. Rather, the specific features and acts are disclosed as exemplary forms of implementing the claims.

What is claimed:

1. A system comprising:

one or more processors;

memory coupled to the one or more processors, the memory including one or more modules that are executable by the one or more processors to:

receive, from at least one medical device, medical imaging data associated with a patient medical examination;

analyze the medical imaging data to extract one or more medical characteristics, the one or more medical characteristics including at least a patient identifier and medical result data;

generate interpretation data associated with the patient medical examination, based at least in part on analysis of the medical imaging data;

receive, from a client device, a search request for the medical imaging data;

generate a graphical representation of the medical imaging data, based at least in part on the interpretation data;

overlay the graphical representation onto a template schematic representation of an organ system associated with the medical imaging data; and transmit, to the client device, an instance of the graphical representation overlaid onto the template schematic representation of the organ system.

2. The system of claim 1, wherein the at least one medical device corresponds to an x-ray device, a magnetic resonance imaging (MRI) device, a computed tomography (CT) device, an ultrasound device, or a Positron Emission Tomography (PET) device.

3. The system of claim 1, wherein to analyze the medical imaging data further includes employing optical character recognition to identify the one or more medical characteristics from text and images of the medical imaging data.

4. The system of claim 1, wherein to analyze the medical imaging data further includes analysis of graph data that represents pertinent medical characteristics captured by the medical imaging data, the pertinent medical characteristics including at least one of stenosis, blood flow velocity, or plaque characteristics.

5. One or more non-transitory computer-readable media storing computer-executable instructions that, when executed on one or more processors, cause the one or more processors to perform acts comprising:
  receiving, from a client device, a search request for medical imaging data and corresponding interpretation data, the search request including at least one medical result identifier;
  retrieving, from a data store, the medical imaging data and the corresponding interpretation data that is associated with the at least one medical result identifier;
  identifying a template schematic representation of an organ system that is associated with the medical imaging data, the template schematic representation including patient-specific template images from prior medical examinations, or template images associated with a population of patients;
  generating a graphical representation of a pertinent medical characteristic associated with the medical imaging data, based at least in part on the corresponding interpretation data; and
  overlaying the graphical representation of a pertinent medial characteristic onto the template schematic representation; and
  transmitting, to the client device, an instance of the graphical representation of the pertinent medical characteristic overlaid onto the template schematic representation.

6. The one or more non-transitory computer-readable media of claim 5, wherein the medical result identifier corresponds to a pertinent medical characteristic of medical imaging data, the pertinent medical characteristic including one or more of stenosis, blood flow velocity, or plaque characteristics.

7. The system of claim 1, wherein to analyze the medical image data further includes at least one of a feature-based object recognition algorithm or an appearance-based object recognition algorithm.

8. The system of claim 1, wherein the one or more modules are further executable by the one or more processors to:
  aggregate the medical imaging data and the interpretation data into a database record; and
  store, within a data store, the database record.

9. The system of claim 8, wherein the one or more modules are further executable by the one or more processors to:
  determine an identifier that is associated with the medical imaging data, the identifier corresponding to one of the patient identifier, the organ system, a medical specialty, or a medical imaging device to generate the medical imaging data, and
  wherein, to store the database record within the data store is based at least in part on the identifier.

10. The one or more non-transitory computer-readable media of claim 5, further storing instructions that, when executed cause the one or more processors to perform acts comprising:
  removing personally identifiable data from the medical imaging data and the corresponding interpretation data to create anonymized patient medical data; and
  storing, the anonymized patient medical data in an anonymized data store.

11. The one or more non-transitory computer-readable media of claim 10, further storing instructions that, when executed cause the one or more processors to perform acts comprising:
  receiving an additional search request for medical imaging data that is associated with the population of patients; and
  retrieving, from the anonymized data store, the anonymized patient medical data.

12. The one or more non-transitory computer-readable media of claim 5, further storing instructions that, when executed cause the one or more processors to perform acts comprising:
  receiving, from at least one medical device, the medical imaging data;
  analyzing the medical imaging data to extract one or more medical characteristics, the one or more medical characteristics including the at least one medical result identifier; and
  generating the corresponding interpretation data based at least in part on analysis of the medical imaging data.

13. The one or more non-transitory computer-readable media of claim 12, further storing instructions that, when executed cause the one or more processors to perform acts comprising:
  aggregating the medical imaging data and the corresponding interpretation data into a database record; and
  storing, within the data store, the database record.

14. The one or more non-transitory computer-readable media of claim 12, wherein the at least one medical device corresponds to an x-ray device, a magnetic resonance imaging (MRI) device, a computed tomography (CT) device, an ultrasound device, or a Positron Emission Tomography (PET) device.

15. The one or more non-transitory computer-readable media of claim 12, wherein analyzing the medical imaging data further includes employing optical character recognition to identify the one or more medical characteristics from text and images of the medical imaging data.

16. A computer-implemented method, comprising:
  under control of one or more processors:
    receiving, from a medical device, medical imaging data associated with a medial result identifier;
    analyzing the medical imaging data to generate interpretation data;
    storing, within a data store, the medical imaging data and the interpretation data;
    receiving, from a client device, a search request for the medical imaging data;
    generating a graphical representation of the medical imaging data, based at least in part on the interpretation data;
    overlaying the graphical representation onto a template schematic representation of an organ system associated with the medical imaging data; and
    transmitting to the client device, an instance of the graphical representation overlaid onto the template schematic representation of the organ system.

17. The computer-implemented method of claim 16, wherein the data store corresponds to a patient data store that includes medical imaging data with personally-identifiable information, and further comprising:
  determining that the search request is associated with an individual patient, and
  retrieving, from the patient data store, the medical imaging data and the interpretation data, and
  wherein, generating the graphical representation is based at least in part on the medical imaging data and the interpretation data retrieved from the patient data store.

18. The computer-implemented method of claim 16, wherein the data store corresponds to an anonymized data store, and further comprising:
   removing personally identifiable data from the medical imaging data and the interpretation data to create anonymized patient medical data; and
   storing, within the anonymized data store, the anonymized patient medical data.

19. The computer-implemented method of claim 18, further comprising:
   determining that the search request is associated with a population of patients; and
   retrieving, from the anonymized data store, the anonymized patient medical data, and
   wherein, generating the graphical representation is based at least in part on the anonymized patient medical data.

20. The computer-implemented method of claim 16, wherein the medical device corresponds to an x-ray device, a magnetic resonance imaging (MRI) device, a computed tomography (CT) device, an ultrasound device, or a Positron Emission Tomography (PET) device.

\* \* \* \* \*